United States Patent [19]

Untereker et al.

[11] Patent Number: 5,711,761
[45] Date of Patent: *Jan. 27, 1998

[54] IONTOPHORETIC DRUG DELIVERY

[75] Inventors: Darrel F. Untereker, Cedar; Joseph B. Phipps, Plymouth; Gary A. Lattin, Forest Lake, all of Minn.

[73] Assignee: ALZA Corporation, Palo Alto, Calif.

[ * ] Notice: The term of this patent shall not extend beyond the expiration date of Pat. No. 4,747,819.

[21] Appl. No.: 394,075

[22] Filed: Feb. 24, 1995

Related U.S. Application Data

[62] Division of Ser. No. 101,803, Aug. 2, 1993, Pat. No. 5,415,628, which is a continuation of Ser. No. 891,319, May 29, 1992, abandoned, which is a division of Ser. No. 154,566, Feb. 10, 1988, Pat. No. 5,135,477, which is a continuation-in-part of Ser. No. 665,698, Oct. 29, 1984, Pat. No. 4,747,787, and a continuation-in-part of Ser. No. 665,699, Oct. 29, 1984, Pat. No. 4,747,819.

[51] Int. Cl.$^6$ .................................................. A61N 1/30
[52] U.S. Cl. ................................................................ 604/20
[58] Field of Search ................................ 604/20; 607/115, 607/149, 152, 153

[56] References Cited

U.S. PATENT DOCUMENTS

| | | | |
|---|---|---|---|
| 3,834,373 | 9/1974 | Sato | 128/2.06 E |
| 4,292,968 | 10/1981 | Ellis | 128/207.21 |
| 4,383,529 | 5/1983 | Webster | 604/20 |
| 4,474,570 | 10/1984 | Ariura et al. | 604/20 |
| 4,526,176 | 7/1985 | Bremer et al. | 128/641 |
| 4,602,909 | 7/1986 | Csillik et al. | 604/20 |
| 4,747,819 | 5/1988 | Phipps | 604/20 |

FOREIGN PATENT DOCUMENTS

| | | | |
|---|---|---|---|
| 0082128 | 6/1983 | European Pat. Off. | A61B 5/04 |
| 0029297 | 6/1984 | European Pat. Off. | A61B 5/04 |
| 2509182 | 7/1982 | France . | |
| 2116037 | 9/1983 | United Kingdom | A61K 31/475 |

OTHER PUBLICATIONS

Samarin et al., Physicochemical Study of Iontophoresis, Voprosy Kurotologii, Fizioterapi i Lechebnoi Fizicheskoi Kul'tury 1957, No. 4, pp. 3–7; with translation Chapter 12, Iontophoresis, in Electrokinetischeskie kapillarnykh system: monographicheskiy sbornik. Editor: P A Rebinder, Moscow, USSR Academy of Science, 1956, pp. 310–327; with translation.

Item of The New York Times, Sunday, May 26, 1991: "Refining the Art of Giving Medicine with a Deft Jolt of Electricity".

J. Allergy Clin. Immunol, Dec. 1973, vol. 52, No. 6, pp. 328–333: Richard H. Shereff et al.: "effect of beta adrenergic stimulation and blockade on immediate hypersensitivity skin test reactions".

Acta Anaesthesiologica Scandinavia, Apr. 1984, vol. 28, pp. 209–210: S.B. Arvidsson et al., "Painless Venipuncture, A Clinical Trial of Iontophoresis of Lidocaine for Venipuncture in Blood Donors".

Bulletin–Italian Society of Experimental Biology (Bolletino–Societa Italiana di Biologia Sperimentale). 1983, vol. 50, No. 6, pp. 806–812: G.A. Rossi et al: "Interference of extraneous solute in the ionto–phoresis of salicyclic acid through the skin" (Interferenza di soluti estranci nella iontoforesio dell'acide salicilico attraverso la pelle).

Vladimirov et al., : "Nonpolarized Electrode for the Iontophores of Pencicilin" (Collected works of the V.M. Molotov State Medical Institute in Tomsk and the Tomnsk Oblast Scientific Research Institute of Physical Medication and Health–Resort Treatment), vol. 8, pp. 186–192, 1953. (with English Translation).

(List continued on next page.)

*Primary Examiner*—Mark Bockelman
*Attorney, Agent, or Firm*—D. Byron Miller; Christopher P. Rogers; Steven F. Stone

[57] ABSTRACT

Improved methods of ionophoretic drug delivery are described. By the intentional selection of drug(s) with specific characteristics, of ionotophoresis device, components or both permits the efficiency of drug delivery is increased.

9 Claims, 2 Drawing Sheets

OTHER PUBLICATIONS

Hawley, ed., "Condensed chemical Dictionary", 10th Ed., pp. 390, 782, Van Nostrand Reinhold Co., Inc., New York (1981).

"CRC Handbook of Chemistry and Physics", 58th Ed., 1977–1978, pp. B–110, B–156, B–254, and D–141 to D–143 (1977).

Abramowitsch et al., Chapter 11 in "Treatment by Ion Transfer (Iontophoresis)", pp. 7 to 54, Grune & Stratton, New York (1946).

Teorell T., "Transport Processes in Membranes in Relation to the Nerve Mechanism", Experimental Cell Research, Suppl. 5, pp. 83–100 (1958).

"CRC Handbook of Chemistry and Physics", 73rd Ed., 1992–1993, pp. 8 to 39 (1992).

Levai, "Dionin Iontophoresis by Means of Gelatin Plates" Munchner Medizinische Wochenschrift, No. 50, pp. 1,936 to 1,937, Dec. 13, 1934.

"The Phoresor uses electrical current to delivery local anesthetic through the skin without pain, puncture or risk of infection." Medical electronics, p. 61 (sep. 1979. (Absract only).

Promotional literature on the Drionic device from General Medical Co. (1988); citing 26 years of service.

Ulashtchik, V.S.: Theory and Practice of Medicinal Electrophoresis, Table 50, pp. 145–148, 1976, Minsk. (with English translation).

Korstanje, et al., "Iontophoresis" Pharmaceutisch Weekblad, vol. 117, pp. 1,184–1,188, 1982 (with English Transalation).

Rose, et al., "Introduction to Techniques in Developmental Electrobiology" in Current Topics in Development Biology, vol. 16, Academic Press, p. 24 (1980).

Girya, "Research on the Protective properties of Ion–Exchange Membrane during the Electrophoresis of Medicines". In: Voprosy Kurortolgil I Fizioceraii na Urale (Problems of Health Resort Treatment and Physical Therapy in the Urals), Sverdlovski, 1967, pp. 83–39.

Klare, "Erfahrungen mit Reparil®, Iontophoretic, Phophoretic and Oral Application from the Department for Physical Medicine and Rehabilitation of the Wilhelm Hospital, Vienna, board of Directors": Univ. Dez.Dr. V. Klar Ther. d. Gegenw., 240 to 253 (1968).

Plotze, "Vergleichende Untersuchung uber die Wirkung der Mobilat Gel–Iontophorese bei Erkankungen des Bewegungsapparates" (Test comparison about the effect of the Mobilat Geliontophoresis during illnesses of the Movement Apparatus), Med MSCHR, 30 Jahrgang, Heft 2 (1976), pp. 83–85. (with English translation).

IONTOPHORETIC DRUG DELIVERY

This application is a division of application Ser. No. 08/101,803 filed Aug. 2, 1993, U.S. Pat. No. 5,415,628, which is a continuation of Ser. No. 07/891,319 filed May 29, 1992 now abandoned, which is a division of Ser. No. 07/154,566 filed Feb. 10, 1988, U.S. Pat. No. 5,135,477, which is a continuation-in-part of Ser. No. 06/665,698 filed Oct. 29, 1984, U.S. Pat. No. 4,747,787 and a continuation-in-part of Ser. No. 06/665,699, filed Oct. 29, 1984, U.S. Pat. No. 4,747,819 and benefit of said earlier filed applications is claimed under 35 USC §120.

CROSS-REFERENCE TO RELATED APPLICATION

Cross-reference is made to applicants' concurrently filed, commonly assigned U.S. patent application entitled, "Improved Iontophoresis Apparatus and Methods of Producing Same".

BACKGROUND OF THE INVENTION

This invention relates to methods and apparatus for transdermal medicament delivery and to improvements therein. More specifically, this invention relates to improved methods and apparatus for active (as opposed to passive) transdermal, ambulatory, drug delivery. Yet more particularly, this invention relates to increased efficiency iontophoresis devices or appliances and to improved methods of making and using such devices.

Iontophoresis, according to *Dorland's Illustrated Medical Dictionary*, is defined to be "the introduction, by means of electric current, of ions of soluble salts into the tissues of the body for therapeutic purposes." Iontophoretic devices have been known since the early 1900's. British patent specification 410,009 (1934) describes an iontophoric device which overcame one of the disadvantages of such early devices known to the art at that time, namely the requirement of a special low tension (low voltage) source of current which meant that the patient needed to be immobilized near such source. The device of that British specification was made by forming from the electrodes and the material containing the medicament or drug to be delivered transdermally, a galvanic cell which itself produced the current necessary for iontophoretically delivering the medicament. This ambulatory device thus permitted iontophoretic drug delivery with substantially less interference with the patient's daily occupation.

More recently, a number of U.S. patents have issued in the iontophoresis technology, indicating a renewed interest in this mode of drug delivery. For example, U.S. Pat. No. 3,991,755 issued to Jack A. Vernon et al; U.S. Pat. No. 4,141,359 issued to Stephen C. Jacobson et al; U.S. Pat. No. 4,398,545 issued to Wilson; U.S. Pat. No. 4,250,878 issued to Jacobsen disclose examples of iontophoretic devices and some applications thereof. The iontophoresis process has been found to be useful in the transdermal administration or introduction of medicaments or drugs including lidocaine hydrochloride, hydrocortisone, acetic acid, fluoride, penicillin, dexamethasone sodium phosphate and many other drugs. Perhaps the widest use of iontophoresis is that of diagnosing cystic fibrosis by using pilocarpine nitrate iontophoresis. The pilocarpine nitrate stimulates sweat production; the sweat is collected and analyzed for its chloride content to detect the presence of the disease.

In presently known iontophoretic devices, at least two electrodes are generally used. Both these electrodes are disposed so as to be in intimate electrical contact with some portion of the skin of the body. One electrode, called the active electrode, is the electrode from which the ionic substance, medicament, drug precursor or drug is delivered or driven into the body by electrical repulsion. The other electrode, called the indifferent or ground electrode, serves to close the electrical circuit through the body. In conjunction with the patient's skin contacted by the electrodes, the circuit is completed by connection of the electrodes to a source of electrical energy, e.g., a battery, or appropriately modified household current. For example, if the ionic substance to be driven into the body is positively charged, then the positive electrode (the anode) will be the active electrode and the negative electrode (the cathode) will serve to complete the circuit. If the ionic substance to be delivered is negatively charged, then the negative electrode will be the active electrode and the positive electrode will be the indifferent electrode.

Furthermore, existing iontophoresis devices generally require a reservoir or source of the ionized or ionizable species (or a precursor of such species) which is to be iontophoretically delivered or introduced into the body. Examples of such reservoirs or sources of ionized or ionizable species include a pouch as described in the previously mentioned Jacobsen U.S. Pat. No. 4,250,878, or the preformed gel body of U.S. Pat. No. 4,383,529 issued to Webster. Such drug reservoirs, when electrically connected to the anode or the cathode of an iontophoresis device to provide a fixed or renewable source of one or more desired species, are generally used with anodes or cathodes which are substantially electrochemically inert. As is more fully discussed below, utilization of such substantially inert electrodes as contemplated in the prior art has significant disadvantages.

The present invention provides enhanced methods and apparatus for the iontophoretic delivery of ionized or ionizable medicaments e.g., drugs, by means of the intentional selection and utilization of a combination of anode or cathode conductive members or electrodes having specified characteristics and the drug(s) to be delivered. Use of this invention increases the efficiency, safety and acceptability of the iontophoretic drug delivery process.

BRIEF SUMMARY OF THE INVENTION

Briefly, in one aspect, the present invention is a method of iontophoretic drug delivery wherein the drug to be iontophoretically delivered, an electrochemically active component of the drug delivery apparatus, or both, are intentionally selected so that during operation of the device, the production of unwanted species is minimized. In another aspect of this invention, the drug to be iontophoretically delivered, an electrochemically active component of the apparatus or both are intentionally selected to reduce the formation of unwanted water hydrolysis products during operation of the device. In yet another aspect of this invention, the drug to be delivered, an electrochemically active component of the iontophoresis apparatus or both, are intentionally selected so as to reduce the presence of water hydrolysis products after they are formed. As contemplated herein, an electrochemically active component of an iontophoresis device is a part of the device which is oxidized or reduced during iontophoretic drug delivery or which oxidizes or reduces other available species.

The present invention also contemplates improved bioelectrodes particularly suited for use with iontophoresis device or appliance. The improved electrode of this invention provides an iontophoretic device which exhibits enhanced coulombic efficiency in drug delivery processes. The electrode comprises a reservoir containing the medicament to be iontophoretically delivered, the reservoir being in electrical connection with an electrochemically active component, e.g., an active current distribution member, the species produced from the electrochemically active component during operation of the device interacting with the counterion of the medicament of the reservoir during iontophoretic drug delivery so as to minimize the formation and delivery of undesired species, the electrochemically active component being in further electrical connection with a source of electrical energy. In a preferred aspect, the electrode includes means to secure the electrode to the skin so as to permit iontophoretic drug delivery therefrom.

In a further aspect, the present invention is a method of iontophoretic drug delivery having enhanced coulombic efficiency comprising the steps of selecting the ionic species e.g., a drug, to be iontophoretically delivered; incorporating the ionic species into an electrode such as in its medicament reservoir; selecting the composition or construction of either the anode or the cathode of the iontophoresis device to include an electrochemically active component so that electrochemical reaction at the anode or the cathode produces species which interact with the ionic species so as to reduce the formation of undesired ions; placing the selected anode or cathode in electrical connection with the ionic species (e.g., in connection with the reservoir) and with a source of electrical energy; and transdermally delivering the selected ionic species into the body while minimizing the formation and delivery of undesired species.

DETAILED DESCRIPTION OF THE INVENTION

The genesis of this invention was in the realization that known iontophoretic drug delivery processes have an efficiency in the range of about 5% or less and that iontophoretic drug delivery is largely a diffusion dependent process. This means that approximately 95% of the current utilized in known iontophoresis processes is consumed in activities other than delivering the intended drug. For example, much current is wasted by the migration of highly mobile species such as $H^+$, $OH^-$, $\rightarrow Na^+$ and $Cl^-$.

Thus it was realized that iontophoretic drug delivery efficiency would be enhanced if the availability of species which are more mobile than the drug which was to be delivered were minimized. Minimization of the concentration or charge of species which were more easily transported than the intended species (i.e., a drug) is utilized herein to provide enhanced drug delivery. It is the enhanced drug delivery described herein which may permit iontophoresis to become a viable alternative to other drug delivery techniques.

Prior art iontophoretic devices often utilize substantially inert stainless steel, nickel or other nickel and iron alloys as current distribution members or electrodes. During operation of such iontophoretic devices in accordance with prior art iontophoretic drug delivery methods, electrolysis of water occurs. Hydronium ($H^+$) ions are formed at the anode and hydroxide ions ($OH^-$) are produced at the cathode. In addition, gaseous hydrogen and oxygen are evolved at the cathode and anode, respectively. (Use of nickel or nickel-containing alloys e.g., stainless steel, also occasionally results in the formation of nickel ions at the anode. The nickel ions are then free to migrate into the drug reservoir of the device and from there into the body.)

Iontophoretic devices which employ such essentially inert electrodes have several inherent disadvantages. First, they exhibit reduced coulombic efficiency of drug transfer (i.e. of charge species) due to the formation of highly mobile hydronium and hydroxyl ions at the electrodes. In addition, such devices evidence instability of pH in the anodic and cathodic reservoirs and adjacent the skin due to the formation of hydronium or hydroxyl ions and gaseous products (hydrogen and oxygen) at the electrodes. Lastly, as noted above, while prior art iontophoretic electrodes are substantially electrochemically inert some undesirable oxidation of e.g., nickel or other alloy metals, does occur.

These disadvantages means that known iontophoretic devices used according to conventional drug delivery methods have the following drawbacks:

1) Lower coulombic efficiency requires that the battery (or a portable or ambulatory device be larger (i.e. of higher capacity). In addition, the voltage required to maintain a certain therapeutic dose rate becomes larger as the coulombic efficiency becomes smaller.

2) The shift in pH in the cathodic and anodic reservoirs, caused by the electrolysis of water, can cause skin irritation, possible degradation the physical properties of the gel components of the device or change the activity of the drug.

3) The formation of hydrogen and oxygen gas at the electrodes can result in a loss of contact between the electrodes and reservoirs leading to reduced device performance.

4) The oxidation of nickel or other metals at the anode results in the contamination of the anodic reservoir with metal ions which then are free to migrate into the skin and body with possible deleterious effects.

It is to overcome these disadvantages and increase the overall efficiency of the iontophoresis process that the present invention was made.

One method contemplated by the present invention for reducing the formation of undesirable or undesired hydronium ions at an electrode and to reduce contamination of the drug reservoir due to the oxidation of electrode metal is to intentionally select an electrode (e.g., an anode) comprising an electrochemically active or sacrificial component which, when oxidized or reduced during operation of the device, produces a species which immediately reacts with ions (e.g., anions) present in the electrode or available to the electrode e.g., in the drug reservoir (which also may be selected, to form an insoluble salt or neutral chemical compound, e.g. $H_2O$. "Sacrificial" as that term is used herein means that at least a portion of the electrode (whether anode or cathode) is electrochemically oxidized or reduced during transdermal drug delivery. "Electrochemically active", as the term is used herein, means "sacrificial" as defined above, but includes a material that is not itself oxidized or reduced but which participates in oxidation/reduction. The anion or cation present in the drug reservoir can be present as a separately added material or as the counter-ion to an anionic or cationic drug to be delivered. Illustrating this practice of the invention, the chloride (or hydrochloride) form of a positively charged drug ($D^+$) would be chosen to be delivered (e.g., by adding it to the reservoir) and the anode would have a silver electrochemically active component which would be sacrificed by oxidation during iontophoresis. The electrochemically generated silver ions would react with the chloride ion in the drug reservoir to form silver chloride. Thus, it is seen that the design of the sacrificial or electrochemically active component of electrode/drug reservoir system can require the selection of an appropriate electrode material, or electrode construction, drug, drug salt or both.

By this expedient, i.e., precipitation of an insoluble species, silver ions and chloride ions are removed from the drug delivery systems and thus are not available to migrate through the reservoir and into the body and therefore the device is more efficient, requiring less battery energy to deliver the drug. The efficiency of delivery of desired species is increased because unwanted species such as $Ag^+$ and $Cl^-$ are simply removed from the system. Furthermore, production of $H^+$ is minimized or avoided thus minimizing pH variation and $O_2$ production.

In an analogous fashion, if a neutral species is formed from undesired ions (rather than one which precipitates from the system) there is again a net removal of unwanted species since neutral species also would not reduce the efficiency of delivery of charged drug species by migrating in response to electrical currents.

Possible electrode electrochemically active component materials and drug anions for sacrificial electrode devices are numerous, but in general, silver, copper and molybednum metals form insoluble halide salts (e.g. $AgCl$, $AgI$, $AgBr$, $CuCl$, $CuI$, $CuBr$, $MoCl_3$, $MoI_2$) and therefore are possible sacrificial anode candidates for delivery of cationic drugs. In addition, retro and ferricyanides of many metals (e.g., Ag, Sn, Zn, Ni, Mn) are insoluble and therefore combination of these metals with iron cyanide doped reservoirs may provide suitable sacrificial anode/drug reservoir systems. Additional electrodes employing sacrificial anodes would include electrodes having a tin or zinc anode and in which phosphate ions were the counterions to the cationic drug, electrodes having zinc anodes and having oxalate ions as the counterion to the cationic drug and electrodes having copper anodes and citrate ions as the counterions to the cationic drug. As noted above, preferentially, the drug will be compounded with its counterion.

The silver anode/drug chloride sacrificial system is particularly preferred for two reasons. First, silver chloride is highly insoluble and second, many catonic drugs can be purchased in the hydrochloride form which means that the chloride anion in the drug reservoir will be present as the counterion to the drug cation. During operation of an iontophoretic device with a silver anode (e.g., a silver current distribution member) and chloride-containing reservoir, silver is oxidized ($Ag \rightarrow Ag^+ + e^-$) and then reacts with the chloride ion to form insoluble silver chloride near the surface of the silver anode ($Ag^+ + Cl^- \rightarrow AgCl$). Simultaneously, the drug cation migrates from the reservoir into the body with greater efficiency than if the oxidation of water to form hydronium ion were allowed to occur at the anode if the anode were substantially inert i.e., it had no electrochemically active component.

An example of a system where the anion in the drug reservoir is present as an additive is the copper/potassium ferrocyanide system. When $K_3Fe(CN)_6$ is added to the drug reservoir, $FeCN_6^{3-}$ anions are formed. By placing the drug reservoirs in contact with e.g., a copper anode, the insoluble salt, $Cu_3Fe(CN)_6$ will be formed during device operation. However, unlike the silver/chloride system where the drug cation migrates into the body, in this system, potassium ions will be free to migrate from the drug reservoir into the body. Generally speaking, then a further practice of this aspect of the invention would be to employ $D_xFe(CN)_6$ (x is an integer greater than 0), rather than $K_3Fe(CN)_6$, where it is desired to transport a drug, D+ species through the skin without cationic e.g., $K^+$, competition.

In an analagous practice of this invention, negatively charged, anionic drugs may be more efficiently delivered if an electrochemically active component of the cathode is intentionally selected utilizing the precepts of this invention.

An example of a sacrificial cathode electrochemically active material of this invention is chloridized silver. During device operation, the AgCl on the surface of a silver cathode is decomposed to give silver metal and chloride anion ($AgCl + e^- \rightarrow Ag + Cl^-$). The chloride anion is free to migrate, along with any anionic drug, into the body. In this respect, the Ag/AgCl sacrificial cathode is less efficient than the silver/chloride sacrificial anode in that chloride ion is produced and is delivered to the body. However, the beneficial aspects of the Ag/AgCl cathode include, (a) no hydrogen gas formation and (b) no hydroxyl anions produced at the cathode.

One skilled in this art will recognize that a sacrificial cathode of this generic type generally comprises a metallic salt in contact with a metal cathode. Furthermore, device operation must result in the decomposition of the metallic salt to form a metal in reduced form plus an anion. If both these conditions are met, in this practice of the present invention, anionic drugs are delivered with mitigation of pH changes.

The use of a sacrificial cathode as herein described in conjunction with an anionic drug specifically selected so that the counterion will react with the anion being produced at the cathode to form an insoluble salt or neutral compound, provides an equivalent method for the control of ion transport as outlined for the anode and anodic reservoir.

Two examples of anionic drug ($D^-$) which could be intentionally selected for with an Ag/AgCl cathode (these drugs would likely be dispersed or dissolved in the ion drug reservoir) are silver or copper salicylate. In this system, chloride ions formed at the cathode are free to react with silver or copper ions in the drug reservoir to form an insoluble salt thus allowing the negatively charged $D^-$ anion to migrate into the body without anionic competition.

In yet another method contemplated by the present invention to minimize the formation of hydronium and hydroxide ions which consume current and reduce efficiencies, an intercalation-type cathode or anode is employed. Intercalation electrodes have the property of being capable of absorbing or desorbing alkali metal ions e.g., sodium and potassium, into their structure as the electrodes are oxidized or reduced. Examples of such intercalation compounds would include sodium vanadate and sodium tungstate. The use of intercalation-type cathode or anode materials is particularly advantageous in that the formation of hydroxyl and hydronium ions is minimized along with a decline in the production of hydrogen or oxygen gas.

It is to be recognized that electrodes comprising intercalation-type materials may be used either on the anode or the cathode of the iontophoresis device and thus can deliver either positively or negatively charged drugs. This can be illustrated for sodium tungstate, above, where the anodic reaction would be:

For a cathodic reaction,

For cathodic electrodes, incorporation of the alkali ion in the drug reservoir would be required. Preferably, this is accomplished by compounding the anionic drug with the alkali metal ion as its counterion. Other suitable intercalation type materials may include graphite, beta alumina, organometallic compounds, transition metal dichalcogenides, prussian blue, polyaniline, polypyrrole, and polyacetyline.

Figure 2:
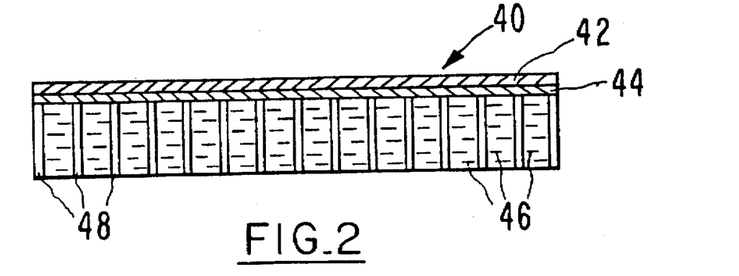
FIG. 2 is a cross-sectional view of a second iontophoresis electrode according to the present invention.
Figure 3:
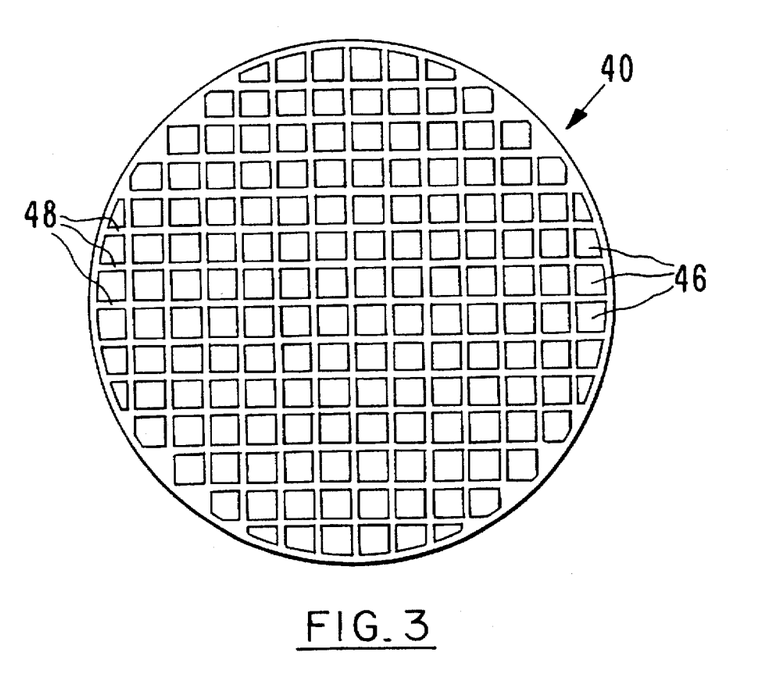
FIG. 3 is a lower, plan view of the iontophoresis electrode of FIG. 2.

In another practice of the present invention, an intercalation-type electrode may be combined with a segmented reservoir to provide an electrode which provides a more even current distribution and minimizes the possibility of iontophoretic burns. FIG. 2 illustrates the side view of such an electrode. The electrode 40 includes a conductive member 42 which has on its surface an intercalation-type compound 44. This compound is in contact with the drug containing gel 46 located in individual compartments within the electrode, separated from each other by walls or dividers 48, which prevent any substantial horizontal ionic migration. FIG. 3 shows a bottom plan view of the electrode of FIG. 2, illustrating how the walls 48 divide the drug containing gel 46 into different isolated compartments.

Intercalation-type compounds have two particular benefits in conjunction with the compartmentalized electrode. First, the rate of intercalation of ions into or out of the intercalation compound limits the current flow and thus sets a maximum current density. The rate of intercalation into or out of the electrode may be controlled by the type of polymer chosen for the drug reservoir and by the polymer morphology. In addition, after a predetermined number of ions have intercalated into or out of the intercalation compound in a particular area, the compound polarizes and becomes non-conductive in that area. In conjunction with a segmented electrode, this results in an automatic shut off of the current flow through the compartment or compartments in that area, after a predetermined amount of current flow.

The compartmentalized reservoir illustrated in FIGS. 2 and 3 is also believed useful in conjunction with the combinations of current distributing members and ionic drugs described elsewhere in the present application. Use of intercalation-type compounds in the absence of the compartmentalized reservoir is also believed beneficial, as discussed above. However, combining the two is believed to provide a significant additional benefit which neither of the two elements individually can provide.

In the absence of the compartmentalized electrode, use of an intercalation compound will still limit the total overall current flow, but horizontal migration of the ions through the gel could still result in hot spots. Use of highly resistive gel for the drug reservoir would permit limiting the overall current density, but at the expense of battery life. The compartmentalized reservoir alone would prevent substantial horizontal migration of ions, but still would allow hot spots to form in individual compartments limited only by the resistance of the reservoir gel. The combination of the intercalation-type electrode with the compartmentalized reservoir allows for the use of a low impedance polymer gel to prolong battery life while retaining the ability to shut off areas of the electrode having unduly high current density and thereby avoid iontophoretic burns.

Figure 4:
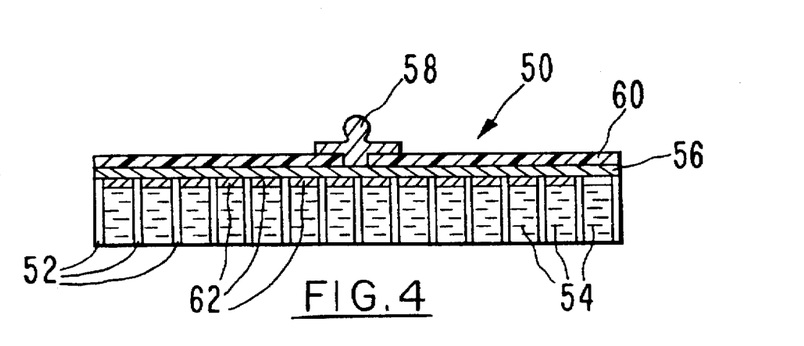
FIG. 4 is a cross-sectional view of a third iontophoresis electrode according to the present invention.

A compartmentalized electrode designed similar to that illustrated in FIGS. 2 and 3 is particularly beneficial when combined with a compartmentalized sacrificial electrode. FIG. 4 shows a cross section of such an electrode 50. The electrode 50 is provided with a multiplicity of individual electrode compartments, separated by compartment walls 52, which are impermeable to the passage of ions. Within each compartment is located the drug reservoir gel 54, containing the ionic drug to be delivered. The electrode is provided with a conductive current distribution member 56, which is adapted to be coupled to a source of direct electrical current via electrical connector 58. An insulative backing 60 covers the current distribution member 56. Within each compartment is located a sacrificial electrode material. For example, in systems for delivery of a positive drug, this may be a silver mesh or foil coating 62, applied to the current distribution member 56. It is important to note that the sacrificial electrode material 62 is compartmentalized within the individual electrode compartments, and does not extend from one compartment to another.

An electrode fabricated in this fashion, has an effect similar to that accomplished by the combination of intercalation compound with a compartmentalized electrode discussed above in conjunction with FIGS. 2 and 3. In the case of an electrode adapted to deliver a positive drug, the electrode would operate as follows. The cationic drug ($D^+$) is compounded in its chloride form, within the individual gel compartments 54. If one of the compartments experiences excessively high current drain, for example due to a breach or flaw in the skin in contact with that cell, the current flowing through that compartment would convert the sacrificial silver 62 to silver chloride more quickly than in surrounding cells. After the silver is completely converted to silver chloride, the current through that compartment would decrease substantially. This reduction in current flow is believed beneficial in avoiding iontophoretic burns, which might otherwise occur in the area of the breach or flaw in the skin.

In yet another practice of the instant invention in which the overall coulombic efficiency of a given iontophoretic drug delivery device is enhanced, a metallic or amalgam electrode is employed optionally in conjunction with the addition of specific metal cations to the drug reservoir i.e., optionally with selection of a drug having a specific metal cation. In this context, lead, mercury and mercury/cadmium amalgams may be used in cathodic electrodes. In this practice of the amalgam electrode is consumed during electrochemical discharge of the device, and it reacts with a species intentionally made available to the electrochemical oxidation/reduction product of the amalgam, e.g., by adding a selected drug to the system such as in the drug reservoir. Thus, as in the context described above, the amalgam material herein described is electrochemically reacted and undesired, highly mobile, charged species are consumed or removed. As with the intercalation-type cathode materials discussed above, the production of hydroxyl and hydronium ions during electrochemical discharge also is reduced. Again pH stability is obtained, thus increasing the overall stability and efficiency of the drug delivery device.

In yet a further method for preventing the formation of hydroxyl ions and hydrogen gas at the cathode is to intentionally select an anionic drug whose counterion is an easily reducible metal such as silver or copper. During operation of a device whose reservoir contains such a metal species, the metal ion is reduced to form the neutral metal and the drug anion is free to migrate and carry charge toward the anode. To generalize, any reducible metal form of the anionic drug of interest may be selected. The metal ion of the drug is reduced to a neutral species, i.e., it is plated out or effectively immobilized, and the drug anion is free to migrate and carry charge toward the anode and into the body.

To this point, the present invention has been described in terms of specific selection of drugs or electrode materials so that the formation of water hydrolysis products (and the problems thereby created) are minimized. However, the present invention is not limited to electrode material/drug selections where electrode component is electrochemically oxidized or reduced during operation of the iontophoresis device. The method of this invention may be practiced with presently available "inert" electrodes if it is realized that their efficiency may be significantly enhanced by the judicious, intentional selection of the drug to be delivered.

Generally speaking, the use of inert electrodes to deliver drugs is accomplished by selecting either the basic e.g., ($OH^-$ or amine) or acid ($H^+$) form of the drug to be incorporated into the reservoir, depending upon whatever an anionic or cationic form of the drug is to be delivered. Weak acid or weak base forms constitute a preferred class of such drugs. For example, oxidation of water proceeds according to the half reaction, $H_2O \rightarrow 2H^+ + \frac{1}{2}O_2 + 2e$. Thus if the basic form of the drug (DOH) is incorporated into the reservoir, the reaction $H^+ + DOH \rightarrow H_2O + D^+$ would occur, preferably in the drug reservoir. By this choice of drug form or drug precursor, hydronium ion is removed by conversion to the neutral species, water, and the concentration of $D^+$ is increased. In addition, if a drug in its uncharged free-base form, D, were incorporated into the drug reservoir, then the use of an "inert" electrode to produce hydronium ion, via oxidation of water, would lead to the formation of the charged drug species $DH^+$ by the reaction $D + H^+ \rightarrow DH^+$. By this method, hydronium ion is removed by protonation of the drug and the concentration of the desired species $DH^+$ is increased. A particularly useful class of drugs which would behave in the fashion described above are tertiary amines ($R_3N$). Specific examples of such drugs are propranolol, nadolol, and metoprolol. Conversely, the reduction of water occurs according to the half reaction, $H_2O + e^- \rightarrow OH^- + \frac{1}{2}H_2$. If it is desired to deliver an anionic drug ($D^-$), the acid form of the drug (DH) should be incorporated into the reservoir. The reaction $OH^- + HD \rightarrow H_2O + D^-$ would occur, thereby removing hydroxyl ions and increasing $D^-$ concentration. This application of the present invention suggests that if either a desired acid or basic form of a specific ionically delivered drug is not available, synthesis for purposes of enhanced iontophoretic drug delivery could be accomplished.

Two observations should be made regarding the description of the present invention in the previous paragraph. First, as described, an inert electrode is intentionally employed to oxidize or reduce water. The electrochemically active component of the drug delivery device (e.g., a stainless steel or platinum electrode component) in the iontophoretic drug delivery process without itself being electrochemically changed or consumed. Second, even though undesirable hydroxyl and hydronium ions are formed, deletrious pH changes are minimized and hydronium ions and hydroxyl ions are converted to neutral water. In this practice of the invention, the production of gaseous species i.e., $H_2$ and $O_2$, occurs and thus the sacrificial methods earlier described should be chosen if gas. evolution is to be avoided.

Figure 1:
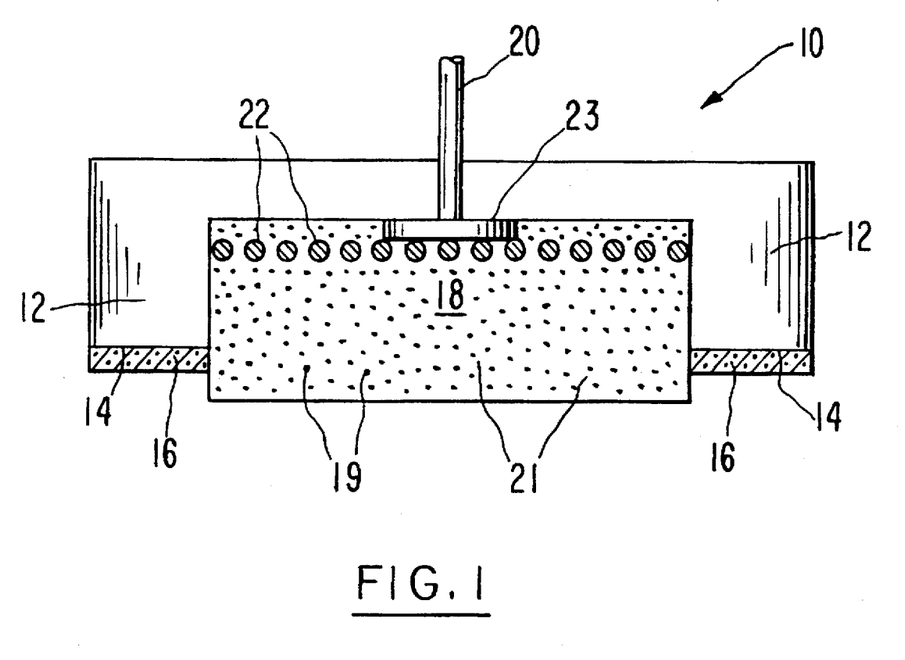
FIG. 1 is a cross-sectional review of a first iontophoresis electrode according to the present invention.

Reference is now made to FIG. 1 included herewith. In the figure, there is depicted, schematically, in cross section, a single substantially, circular electrode 10 which is intended for use in an iontophoretic drug delivery device. It is to be understood that electrode 10 is but one of the two electrodes necessary to successful operation of an iontophoresis device and that the necessary source of electrical energy is also not depicted herein.

Again referring to FIG. 1, electrode 10 comprises a support or housing 12 which is generally "U" shaped and which is preferably flexible. In a preferred embodiment, support 12 is produced from self-supporting polymeric foam. In this practice of the invention, perimeter surface 14 of housing 12 would optionally have disposed thereon a skin-compatible, pressure-sensitive, biomedical adhesive 16 which is intended to hold the electrode in place on the patient's skin during iontophoretic drug delivery. The iontophoresis device may be held in place by other means, e.g., a strap, in which instance adhesive 16 would not be needed. Thus it is to be understood, as depicted, electrode 10 contemplates delivery of drug generally toward the bottom of the page.

With further reference to FIG. 1, there is shown a drug reservoir 18 which, in this practice of the invention, is a gel or gel matrix 21 containing the ionic drug species 19 which is to be transdermally introduced across the skin barrier. In a preferred practice of the invention, the self-supporting, skin-compatible gel matrix 21 for the drug would contain sufficient drug 19 so that approximately a one molar solution (applying the definition of a molarity from solvent-solute interactions) would result. Drug concentrations (in the reservoir) in the range of 0.02M to 1.0M or more can be employed in the practice of this invention. In a preferred practice, the lower reservoir drug concentration ranges (e.g., less than about 0.5 molar) can be used in the efficient devices described herein. It should be noted that any of a number of possible gel matrices may be employed, those being described in the previously mentioned Webster patent comprising a particularly preferred practice of this invention. Agar or polyvinylpyrolidone gels also are advantageously employed herein.

Also in FIG. 1, there is depicted an exterior connector 20 which in this embodiment is a wire. Exterior connector 20 is in further electrical contact with a current distribution member comprising a tab or plate 23 in electrical contact with an optional screen 22. In this embodiment, the current distribution member would comprise silver. (The current distribution member need not be pure silver. An exterior layer of silver is all that is needed.) The silver screen is optionally included only to increase the surface area of the current distribution member.

Thus, in operation, an external source of electrical energy (not shown) would be connected to exterior connector 20 which is, in turn, electrically connected to the silver current distribution member 22, 23.

It should be noted and with reference to the cathodic description of the sacrificial electrode described above that the silver current distribution member shown could be a silver/silver chloride cathode. Electrode 10, as depicted, would be placed in contact with a patient's skin and pressed with sufficient firmness so that pressure sensitive adhesive 16 would hold the drug reservoir 18 in contact therewith by means of flexible housing 12. Silver tab 20 would be electrically connected to a source of electrical energy, preferably a small battery. Utilization of a battery permits iontophoretic drug delivery without substantial interference with the normal activities of the patient.

It is within the contemplation of the present invention that stationary electrical supply sources be employed in which case it would likely be necessary for the patient to be substantially immobilized. Although not depicted, a second indifferent or cooperating electrode would then be placed in contact with the patient's skin at a site separate from but electrically adjacent to the site on which electrode 10 has been placed. Upon connection to a source of electrical energy, migration of charged species from reservoir 18 would occur. In this embodiment of the invention, assuming the reservoir contains therein propranolol hydrochloride or lithium chloride, the silver tab 23 and silver screen 22 anode would be electrochemically consumed to produce silver ions as above described. These silver ions would react immediately with chloride ions which are also present to produce a neutral, substantially insoluble species. In this manner, enhanced delivery or propranolol or lithium would occur due to the fact that little hydrolysis occurs. The silver chloride precipitation reaction removes silver and chloride ions from the reservoir, thus further enhancing efficiency.

Heretofore, the discussion has focused upon the use of iontophoresis to treat humans. Obviously, the invention herein disclosed could be used with animals and should not be limited to humans.

The instant invention will now be illustrated by the following examples which should not be employed so as to limit the scope of this invention:

EXAMPLE I

Description of the Experimental Procedure

In-vivo studies of iontophoretic drug delivery were run on New Zealand white rabbits. As indicated, the rabbits were in some studies sedated as with pentobarbital, and others were merely constrained. The sedation studies generally were conducted for a time period not exceeding 7 hours whereas the "constrained" studies were run for time periods up to 30 hours. Each rabbit was used in a particular study only once.

As is more completely described below, an iontophoretic device employing an electrode as shown and described in FIG. 1 was used to introduce lithium, salicylate, propranolol or sodium chloride into the rabbits. The gel "reservoir" contained approximately a 1 molar concentration of each of the respective drugs. The device employed a silver anode and a silver/silver chloride cathode as described above.

The iontophoretic device was placed posteriorly on the rabbit, the hair having been clipped and removed with a dipilatory. The device was then attached by means of an adhesive for the duration of the experiment. During the experimental procedure, blood samples were removed from the subject rabbits. Where rabbits were anesthetized, blood samples were removed from their inferior vena cava by means of a catheter inserted into the femoral vein. For the experiments employing constrained (rather than anesthetized) rabbits, blood samples were pulled from the heart by means of a catheter inserted into the marginal vein of the rabbit's ear. The samples thus withdrawn then were analyzed for the drug which was iontophoretically introduced therein.

EXAMPLE II

Description of the Data Treatment

Employing the experimental procedure described in Example I, the drugs of interest were iontophoretically introduced into rabbits. Blood samples were withdrawn as described and analyzed, the concentration of the respective drugs being plotted as a function of time. The data so obtained then was fit to the expression $$C = B^{(1-exp(-K_i t))}$$

where "C" is the concentration of drug in the rabbit's blood at a particular time; "B" is the steady state drug concentration, i.e. the highest concentration achieved when drug input and drug elimination are in equilibrium; $K_i$ is the iontophoretic decay constant; and "t" is time. Tables 1, 2 and 3 indicate values of these parameters for a number of runs (each "run" corresponding to numbers obtained from a given rabbit, indicated by letter, on a given day, indicated by number). The drugs delivered in Tables 1, 2 and 3 were lithium ion, salicylate ion and propranolol ion, respectively.

TABLE 1

Lithium Drug Delivery Parameters

| | | Best Fit Parameters | | | | | Efficiency | |
|---|---|---|---|---|---|---|---|---|
| Run No. | Current (mA) | B (mg/L) | $K_i$ (hr$^{-1}$) | $C_o$ (mg/L) | $K_e$ (hr$^{-1}$) | $V_d$ (liters) | $E_r$ (%) | $E_c$ (%) |
| 323A | 10 | 3.0 | 0.66 | | 0.16 (a) | 1.47 (b) | 27 | 24 |
| 323B | 0 | 0.94 | 0.26 | | 0.16 (a) | 1.47 (b) | | |
| 402C | 20 | 5.2 | 0.31 | | 0.16 (a) | 1.32 (b) | 21 | 20 |
| 403A | 5 | 6.0 | 0.77 | | 0.16 (a) | 1.37 (b) | 102 | 79 |
| 403B | 10 | 4.4 | 0.84 | | 0.16 (a) | 1.52 (b) | 41 | 36 |
| 403C | 20 | 8.7 | 0.60 | | 0.16 (a) | 1.62 (b) | 44 | 41 |
| 409A | 30 | 16.7 | 0.31 | | 0.16 (a) | 1.53 (b) | 53 | 51 |
| 409B | 20 | 7.0 | 0.79 | | 0.16 (a) | 1.56 (b) | 34 | 32 |
| 409C | 10 | 6.6 | 0.29 | | 0.16 (a) | 1.59 (b) | 65 | 57 |
| 425A | 0 | — | — | — | 0.12 | | | |
| 425C | 0 | — | — | 1.41 | 0.09 | | | |
| 510A | 1 | 0.3 | — | | 0.16 (a) | 1.63 (b) | 30 | |
| 510B | 5 | 1.0 | 0.51 | | 0.16 (a) | 1.89 (b) | 23 | |
| 510C | 5 | 4.0 | 0.16 | | 0.16 (a) | 1.82 (b) | 90 | 70 |
| 611A | 0 | 3.0 | 0.82 | 2.61 | 0.14 | 1.25 | | |
| 611B | 0.5 | 0.27 | 0.19 | 1.97 | 0.19 | 1.66 | 66 | 17 |
| 611C | 2 | 1.6 | 0.27 | 2.17 | 0.16 | 1.51 | 75 | 44 |
| 619F | 0.5 | 3.0 | 1.72 | | 0.16 (a) | 1.20 (b) | 445 | 116 |
| 619G | 0.5 | 2.9 | 1.06 | 2.62 | 0.27 | 1.25 | 766 | 200 |
| 619H | 0 | 2.1 | 1.13 | | 0.16 (a) | 1.40 (b) | | |
| 619I | 1 | 0.71 | 0.20 | | 0.16 (a) | 1.35 (b) | 59 | 24 |
| Average | | | 0.54 | | 0.16 | | | 43 (c) |
| S.D. | | | ±0.32 | | +0.06 | | | ±20 | a) assumed value based on average $K_e$.
b) assumed value based on 0.49 × body weight in kg.
c) average for currents greater than or equal to 1 mA.

TABLE 2

Salicylate Drug Delivery Parameters

| Run No. | Current (mA) | Best Fit Parameters ||||| Efficiency ||
|---|---|---|---|---|---|---|---|---|
| | | B (mg/L) | $K_i$ (hr$^{-1}$) | $C_o$ (mg/L) | $K_e$ (hr$^{-1}$) | $V_d$ (liters) | $E_r$ (%) | $E_c$ (%) |
| 323A | 10 | 157 | 0.36 | | 0.25 (a) | 0.72 (b) | 55 | 47 |
| 323B | 0 | 60.4 | 0.53 | | 0.25 (a) | 0.72 (b) | | |
| 402C | 20 | 130 | 2.35 | | 0.25 (a) | 0.65 (b) | 21 | 19 |
| 403A | 5 | 182 | 0.91 | | 0.25 (a) | 0.68 (b) | 121 | 90 |
| 403B | 10 | 96.8 | 1.23 | | 0.25 (a) | 0.75 (b) | 35 | 30 |
| 403C | 20 | 173 | 1.47 | | 0.25 (a) | 0.80 (b) | 34 | 31 |
| 409A | 30 | 204 | 0.93 | | 0.25 (a) | 0.76 (b) | 25 | 24 |
| 409B | 20 | 109 | 3.43 | | 0.25 (a) | 0.77 (b) | 21 | 19 |
| 409C | 10 | 85.6 | 0.98 | | 0.25 (a) | 0.78 (b) | 33 | 28 |
| 425A | 0 | | | | 0.46 | | | |
| 425C | 0 | | | 320 | 0.18 | 0.63 | | |
| 510A | 1 | 4 | | | 0.25 (a) | 0.80 (b) | 16 | |
| 510B | 5 | 17.1 | 0.86 | | 0.25 (a) | 0.93 (b) | 16 | |
| 510C | 5 | 37.6 | 0.36 | | 0.25 (a) | 0.90 (b) | 33 | 25 |
| 611A | 0 | 45.0 | 0.16 | 275 | 0.31 | 0.62 | | |
| 611B | 0.5 | 32.3 | 0.09 | 207 | 0.23 | 0.83 | 241 | 55 |
| 611C | 2 | 73.6 | 0.32 | 187 | 0.22 | 0.92 | 146 | 79 |
| 619F | 0.5 | 40 | | | 0.25 (a) | 0.59 (a) | 231 | 52 |
| 619G | 0.5 | 46.0 | 1.05 | | 0.30 | 0.54 | 291 | 66 |
| 619H | 0 | 12 | | | 0.25 (a) | 0.68 (b) | | |
| 619I | 1 | 37.9 | 0.94 | | 0.25 (a) | 0.66 (b) | 122 | 45 |
| Average | | | 0.73 | | 0.25 | | | 28 (c) |
| S.D. | | | ±0.42 | | ±0.06 | | | ±9 | a) assumed value based on average $K_e$
b) assumed value based on 0.24 × body weight in kg.
c) average for currents ≧5 mA

TABLE 3

Propranolol Drug Delivery Parameters

| Run No. | Current (mA) | Best Fit Parameters ||||| Efficiency ||
|---|---|---|---|---|---|---|---|---|
| | | B (mg/L) | $K_i$ (hr$^{-1}$) | $C_o$ (mg/L) | $K_e$ (hr$^{-1}$) | $V_d$ (liters) | $E_r$ (%) | $E_c$ (%) |
| 613D | 0.5 | 0.13 | 0.30 | 0.08 | 0.40 | 21.2 | 23 | 16 |
| 613E | 2 | 0.11 | 0.24 | 0.08 | 0.40 | 22.3 | 5 | 3 |
| 627J | 0 | 0 | | 0.17 | 0.44 | 10.7 | — | — |
| 627K | 0.5 | 0.08 | 0.16 | 0.33 | 0.40 | 5.3 | 3 | 0 |
| 627L | 1 | 0.24 | 0.43 | 0.15 | 0.30 | 11.7 | 9 | 6 |
| 705N | 0.5 | 0.05 | 0.35 | 0.19 | 0.61 | 9.2 | 6 | 0 |
| 705O | 0.5 | 0.23 | 0.30 | — | 0.39 (a) | 11.4 (b) | 21 | 14 |
| 705P | 1.0 | 0.17 | 0.26 | 0.08 | 0.47 | 22.3 | 18 | 15 |
| 705Q | 1.0 | 0.15 | 0.28 | — | 0.39 (a) | 9.6 (b) | 6 | 3 |
| 724R | 0 | 0.35 | 0.14 | 0.24 | 0.39 | 7.2 | — | — |
| 724S | 0.5 | 0.13 | 0.30 | — | 0.39 (a) | 15.1 (b) | 16 | 9 |
| 724T | 0 | 0.19 | 0.25 | 0.21 | 0.46 | 8.5 | — | — |
| 724U | 1.0 | 0.25 | 0.32 | 0.17 | 0.22 | 10.6 | 6 | 3 |
| 801V | 0.5 | 0.11 | 0.56 | 0.08 | 0.24 | 21.7 | 12 | 5 |
| 801W | 1.0 | 0.24 | 0.18 | — | 0.39 (a) | 10.2 (b) | 10 | 7 |
| 801X | 0 | 0.05 | 0.63 | — | 0.39 (a) | 10.9 (b) | — | — |
| 801Y | 0 | 0.06 | 0.50 | 0.16 | 0.33 | 10.9 | — | — |
| Average | | | 0.32 | | 0.39 | | | 6.8 |
| S.D. | | | ±0.14 | | ±0.11 | | | ±5.6 | a) value based on average $K_e$
b) value based on 5.3 × body weight in kg.

EXAMPLE III

For some of the rabbits tested, a known amount of a given drug was administered intravenously and the consumption of the drug by the animal was monitored as a function of time. From these data, values for the drug elimination decay constant ($K_e$) and the initial drug concentration ($C_o$) were determined by plotting the natural logarithm of concentration (lnC) versus time. Once the value of $C_o$ and the intravenous dosage has been determined, the volume of distribution ($V_d$) was calculated using the expression $V_d = \text{Dose}/C_o$ Tables 1, 2 and 3 list the values of $C_o$, $K_e$ and $V_d$ as they were determined or estimated for each run.

EXAMPLE IV

The parameters listed in Tables 1, 2 and 3 can be used to estimate the efficiency of drug delivery. An estimate of the steady-state drug delivery rate ($R_d$) can be made by multiplying the plateau drug concentration (B) by the volume of distribution ($V_d$) and the drug elimination decay constant ($K_e$), that is, $$R_d(mg/hr) = B V_d K_e \quad (1)$$

The maximum amount of drug iontophoretically delivered per unit time ($R_t$) can be calculated from the current used during the experiment, that is, $$R_t(mg/hr) = \frac{3600 MI}{F} \quad (2)$$

where M is the molecular weight of the drug ion, I is the current in milliamps and F is Faraday's constant. The efficiency of drug delivery ($E_r$) can be estimated from the ratio $R_d/R_t$ according to the expression $$E_r(\%) = \frac{R_d}{R_t} \times 100 = \frac{B V_d K_e}{(3.73 \times 10^{-4}) MI} \quad (3)$$

Tables 1, 2 and 3 list the efficiencies estimated from the in-vivo rabbit data for each experiment.

It is to be noted that for some of the runs, the value of $E_r$ exceeded 100%. This is possible since $R_d$ includes a contribution due to passive diffusion of the drug through the skin, therefore the ratio $R_d/R_t$ can exceed unity.

EXAMPLE V

Also listed in Tables 1, 2 and 3 is the true efficiency of drug delivery ($E_c$) for each experiment which was calculated by substracting the passive drug delivery rate ($R_p$) from the total drug delivery rate ($R_d$), that is, $$E_c = \frac{100(R_d - R_p)}{R_t} = E_r - \frac{100 R_p}{R_t}$$

The method used to determine the passive diffusion rate for each drug is discussed in Example VI below.

EXAMPLE VI

It was found that total in-vivo drug delivery data, as defined in equation (1) of Example IV, was the sum of two contributions, one passive and the other iontophoretic. Thus, it was found that the rate of drug delivery ($R_d$) could be expressed as $$R_d = R_p + R_i \quad (4)$$

where $R_p$ is the rate of passive drug delivery and $R_i$ is the rate of iontophoretic drug delivery. The rate of passive delivery depends on the area of contact and the drug concentration of the drug reservoir. The rate of iontophoretic delivery is directly proportional to the current used in the experiment, that is, $$R_i = A E_c I$$

where $E_c$ is the efficiency of drug delivery, I is the current and A is a proportionally constant whose value is determined by the molecular weight of the drug.

Substitution of the above expression for $R_i$ into Equation (4) yields $$R_d = R_p + A E_c I \quad (5)$$

By using the data presented in Tables 1, 2 and 3, a plot of $R_d$ versus current can be made for each drug. From the form of Equation (5), it is readily seen that the intercept of a linear least-squares fit of such plots will yield the passive drug diffusion rate ($R_p$) and the slope can be used to calculate the efficiency of drug delivery ($E_c$).

EXAMPLE VII

From the data obtained as described above, a plot of $R_d$ versus current for lithium chloride, sodium salicylate and propanolol hydrochloride was made and a best linear fit obtained. The rates of passive drug delivery for each of these drugs then is determined by the intercept of this "fit". Values of this intercept are listed in Table 4. Also listed in Table 4 is the equivalent current for each drug. The equivalent current for a given drug is the current at which half of the drug delivery would occur via passive diffusion and half would occur iontophoretically.

The slopes of the best linear fit of $R_d$ versus current described above were used to estimate the efficiency ($E_c$) for in-vivo drug delivery. Table 5 compares the efficiency estimated from the in-vivo experiments to those determined from in-vitro drug delivery through excised rabbit skin and through polyvinyl alcohol (PVA) membrane into a 0.1M sodium chloride solution. The in-vitro drug delivery measurements were taken in accordance with using a Franz diffusion cell commercially available from the Crown Glass Company, Somerville, N.J., U.S.A.

The efficiency of in-vitro drug delivery through a PVA membrane is an indication of the relative mobilities of lithium and propanolol with respect to chloride ion, and salicylate with respect to sodium ion. The efficiency of drug transport through a PVA probably represents an upper limit for the efficiency for the gels, electrodes and drug concentrations likely to be used in the in-vivo experiments.

The data presented in Table 4 indicates that lithium and propanolol were transported approximately equally efficiently through excised and viable rabbit skin. Further the data indicates the salicylate was more effectively delivered through viable tissue than through excised skin.

TABLE 4

| | Passive Diffusion Rate | |
|---|---|---|
| Drug | $R_p$ (mg/hr) | Equivalent Current (mA) |
| Lithium | 0.37 | 1.42 |
| Salicylate | 8.8 | 1.71 |
| Propranolol | 0.33 | 0.034 |

TABLE 5

| | In-Vivo and In-Vitro Coulombic Efficiencies | | |
|---|---|---|---|
| | | In-Vitro | |
| Drug | In-Vivo | Rabbit Skin | PVA Gel* |
| Lithium | 35% | 33% | 30% |
| Salicylate | 19% | 6% | 30% |
| Propranolol | 5% | 5% | 11% |

*polyvinyl alcohol

To summarize, while there does appear to be a fair amount of scatter in the in-vivo data, we have found that the methods described herein provide a fairly reproducible method for determining efficiencies and passive drug delivery rates for in-vivo studies. The efficiencies so calculated appear to be in substantial agreement with similar efficiencies computed from in-vitro experiments.

EXAMPLE VIII

A number of anode/cathode drug combinations and drug concentrations were evaluated with respect to their minimization of the production of undesired species. In particular, drug reservoir pH changes were measured, from which the drug hydronium ion delivery rates were computed. The drug passed through a PVA membrane and was delivered into a 0.06M Na Cl. Further, using the mathematical treatment described above, drug delivery efficiencies were determined. Experimental conditions and efficiencies were measured for delivery of lithium ion, potassium ion and salicylate ion as indicated in Tables 6, 7, 8 and 9.

A number of observations may be made about the systems tested. Systems numbered 1-6 of Table 6 are basically prior art systems.

Undesirable water hydrolysis products are produced and thus pB is shown to change fairly substantially as in "pB" column for systems 1, 2 and 3 in Table 7, 1 and 2 of Table 8 and 1 of Table 9.

As evidenced in Tables 7, 8 and 9, hydronium delivery rates were generally higher, and drug delivery efficiencies were generally lower for prior art systems versus systems employing the present invention. For example, systems numbered 1, 2 and 3 in Table 7 may be compared with systems numbered 4–9 in Table 7. Similarly systems 1 and 2 in Table 8 should be compared with 3–6 in Table 8 and system 1 in Table 9 with 2–8 in Table 9.

To summarize, in conjunction with the teaching above, a broadly-based, flexible approach to solving the problem of inefficiency/instability in iontophoretic drug delivery is disclosed, while this disclosure has focused upon two cationic and one anionic drug, it will be appreciated that this invention is broadly applicable to the iontophoresis art. The attached claims should be so broadly construed.

TABLE 7

Comparison of Lithium Drug Delivery Systems*

| Drug | Anode Material | % Drug Delivery Efficiency | Hydronium Delivery Rate(moles/hr) | pH Initial Value | pH After 6 hrs |
|---|---|---|---|---|---|
| 1. LiCl | Platinum | 20.2 | $3.2 \times 10^{-6}$ | 5.9 | 2.6 |
| 2. LiNO$_3$ | Platinum | 22.8 | $2.0 \times 10^{-6}$ | 7.2 | 2.5 |
| 3. LiCl | S. Steel | 29.1 | $1.8 \times 10^{-7}$ | 6.2 | 3.7 |
| 4. LiNO$_3$ | Silver | 28.5 | $5.5 \times 10^{-8}$ | 5.9 | 4.3 |
| 5. LiNO$_3$ | Copper | 25.0 | $<10^{-9}$ | 5.9 | 5.6 |
| 6. LiCl | Silver | 36.7 | $<10^{-9}$ | 6.5 | 6.2 |
| 7. LiCl | Copper | 30.2 | $<10^{-9}$ | 6.1 | 5.5 |
| 8. Li$_2$CO$_3$ | Silver | 29.5 | $<10^{-9}$ | 10.6 | 10.2 |
| 9. LiOH | Platinum | 41.6 | $1.5 \times 10^{-8}$ | 11.5 | 11.3 |

*All results obtained at a current of 1 mA.

TABLE 8

Comparison of Potassium Drug Delivery Systems*

| Drug | Anode Material | % Drug Delivery Efficiency | Hydronium Delivery Rate(moles/hr) | pH Initial Value | pH After 6 hrs |
|---|---|---|---|---|---|
| 1. KCl | Platinum | 33.7 | $1.4 \times 10^{-6}$ | 5.8 | 2.7 |
| 2. K$_3$Fe(CN)$_6$ | Platinum | 28.6 | $2.1 \times 10^{-6}$ | 6.4 | 2.6 |
| 3. KNO$_3$ | Silver | 36.2 | $5.4 \times 10^{-9}$ | 5.8 | 4.3 |
| 4. KCl | Silver | 39.1 | $<10^{-9}$ | 6.0 | 5.6 |
| 5. K$_3$Fe(CN)$_6$ | Silver | 34.3 | $1.0 \times 10^{-8}$ | 6.4 | 5.9 |
| 6. K$_3$Fe(CN)$_6$ | Copper | 33.8 | $8.9 \times 10^{-10}$ | 7.2 | 4.9 |

*All results obtained at a current of 1 mA.

TABLE 6

Summary of Experimental Conditions

| | Drug | Reservoir Concentration (M) | Electrode Material | Electrode Reaction | Neutralization Reaction |
|---|---|---|---|---|---|
| 1. | LiCl | 0.06 | Platinum | $H_2O \rightarrow 2H^+ + \frac{1}{2} O_2 + 2e^-$ | None |
| 2. | LiNO$_3$ | 0.06 | Platinum | " | " |
| 3. | LiCl | 0.06 | S. Steel | " | " |
| 4. | KCl | 0.06 | Platinum | " | " |
| 5. | K$_3$Fe(CN)$_6$ | 0.02 | Platinum | " | " |
| 6. | NaSal | 0.06 | Platinum | $H_2O + e^- \rightarrow OH^- + \frac{1}{2} H_2$ | " |
| 7. | LiNO$_3$ | 0.06 | Silver | $Ag \rightarrow Ag^+ + e^-$ | None |
| 8. | LiNO$_3$ | 0.06 | Copper | $Cu \rightarrow Cu^{++} + e^-$ | " |
| 9. | KNO$_3$ | 0.06 | Silver | $Ag \rightarrow Ag^+ + e^-$ | " |
| 10. | NaSal | 0.06 | Ag/AgCl | $AgCl + e^- \rightarrow Ag + Cl^-$ | " |
| 11. | HSal | Solid | Ag/AgCl | $AgCl + e^- \rightarrow Ag + Cl^-$ | " |
| 12. | Cu(Sal)$_2$ | 0.05 | Silver | $Cu^{++} + 2e^- \rightarrow Cu$ | " |
| 13. | AgSal | 0.04 | Silver | $Ag^+ + e^- \rightarrow Ag$ | " |
| 14. | AgSal | Solid | Platinum | $Ag^+ + e^- \rightarrow Ag$ | " |
| 15. | LiCl | 0.06 | Silver | $Ag \rightarrow Ag^+ + e^-$ | $Ag^+ + Cl^- \rightarrow AgCl$ |
| 16. | Li$_2$CO$_3$ | 0.03 | Silver | $Ag \rightarrow Ag^+ + e^-$ | $2Ag^+ + CO_3 \rightarrow Ag_2CO_3$ |
| 17. | LiCl | 0.06 | Copper | $Cu \rightarrow Cu^+ + e^-$ | $Cu^+ + Cl^- \rightarrow CuCl$ |
| 18. | LiOH | 0.06 | Platinum | $H_2O \rightarrow 2H^+ + \frac{1}{2} O_2 + 2e^-$ | $H^+ + OH^- \rightarrow H_2O$ |
| 19. | KCl | 0.06 | Silver | $Ag \rightarrow Ag^+ + e^-$ | $Ag^+ + Cl^- \rightarrow AgCl$ |
| 20. | K$_3$Fe(CN)$_6$ | 0.02 | Silver | $Ag \rightarrow Ag^+ + e^-$ | $3Ag^+ + Fe(CN)_6^{3-} \rightarrow Ag_3Fe(CN)_6$ |
| 21. | K$_3$Fe(CN)$_6$ | 0.02 | Copper | $Cu \rightarrow Cu^+ + e^-$ | $3Cu^+ + Fe(CN)_6^{3-} \rightarrow Cu_3Fe(CN)_6$ |
| 22. | AgSal | Solid | Ag/AgCl | $AgCl + e^- \rightarrow Ag + Cl^-$ | $Cl^- + AgSal \rightarrow AgCl + Sal^-$ |
| 23. | HSal | Solid | Platinum | $H_2O + e^- \rightarrow OH + \frac{1}{2} H_2$ | $OH^- + HSal \rightarrow H_2O + Sal^-$ |

TABLE 9

Comparison of Salicylate Drug Delivery Systems*

| Drug | Anode Material | % Drug Delivery Efficiency | Hydroxyl Delivery Rate(moles/hr) | pH Initial Value | pH After 6 hrs |
|---|---|---|---|---|---|
| 1. NaSal | Platinum | 25.9 | $4.6 \times 10^{-6}$ | 6.0 | 11.5 |
| 2. NaSal | Ag/AgCl | 27.8 | $<10^{-9}$ | 6.5 | 5.6 |
| 3. HSal | Ag/AgCl | 20.9 | $<10^{-9}$ | 3.5 | 2.9 |
| 4. Cu(Sal)$_2$ | Silver | 28.3 | $<10^{-9}$ | 4.5 | 4.5 |
| 5. AgSal | Silver | 28.2 | $1.0 \times 10^{-7}$ | 8.6 | 8.7 |
| 6. AgSal | Platinum | 24.9 | $3.3 \times 10^{-8}$ | 5.2 | 8.1 |
| 7. AgSal | Ag/AgCl | 25.0 | $2.9 \times 10^{-10}$ | 5.2 | 5.4 |
| 8. HSal | Platinum | 28.1 | $8.6 \times 11^{-10}$ | 2.8 | 3.4 |

*All results obtained at a current of 1 mA.

We claim:

1. An electrotransport method of delivering an ionic drug D+ comprising the steps of:

providing a reservoir comprising DOH dispersed in a polymer gel in electrical communication with an electrochemically active conductive member;

contacting said reservoir to the skin of a patient;

hydrolyzing water in said reservoir producing hydronium ions;

reacting the hydronium ions with the DOH producing an ionic drug, D+; and, electrically transporting D+ through the skin.

2. The method of claim 1 wherein the DOH is lithium hydroxide.

3. An electrotransport method of delivering an ionic drug D− comprising the steps of:

providing a reservoir comprising HD dispersed in a polymer gel in electrical communication with an electrochemically active conductive member;

contacting said reservoir to the skin of a patient;

reducing water in said reservoir producing hydroxyl ions;

reacting the hydroxyl ions with the HD producing an ionic drug, D−; and, electrically transporting D− through the skin.

4. The method of claim 3 wherein the HD is salicylic acid.

5. The method of claims 1 or 3 wherein the electrochemically active conductive member is also sacrificial.

6. The method of claims 1 or 3 wherein the electrochemically active conductive member is an electrode constructed from a material selected from the group consisting of stainless steel and platinum.

7. A method for delivering an ionic drug D−, comprising the steps of:

providing an electrochemically active conductive member in electrical communication with a reservoir containing the ionic drug D− compounded in its acidic form HD, wherein the ionic drug D− is permeable through a reservoir membrane;

contacting the reservoir to the skin of a patient; and applying a negative voltage to said conductive member to reduce water in the reservoir producing hydroxyl ions which react with the acidic form HD of the ionic drug producing water and driving the ionic drug D− through the skin of a patient.

8. The method of claim 7 wherein the electrochemically active conductive member is also sacrificial.

9. The method of claim 7 wherein the electrochemically active conductive member is an electrode constructed from a material selected from the group consisting of stainless steel and platinum.

* * * * *